US012672927B2

(12) United States Patent
Kopp

(10) Patent No.: US 12,672,927 B2
(45) Date of Patent: Jul. 7, 2026

(54) SYSTEM AND METHOD FOR COMPENSATION FOR AN OFF-AXIS PUSH-PULL DRIVE ROD IN A ROBOTICALLY ASSISTED SURGICAL INSTRUMENT

(71) Applicant: Covidien LP, Mansfield, MA (US)

(72) Inventor: Brock Kopp, Colorado Springs, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/855,721

(22) PCT Filed: Apr. 26, 2023

(86) PCT No.: PCT/IB2023/054310
§ 371 (c)(1),
(2) Date: Oct. 10, 2024

(87) PCT Pub. No.: WO2023/223124
PCT Pub. Date: Nov. 23, 2023

(65) Prior Publication Data
US 2025/0248775 A1      Aug. 7, 2025

Related U.S. Application Data

(60) Provisional application No. 63/342,328, filed on May 16, 2022.

(51) Int. Cl.
*A61B 17/072* (2006.01)
*A61B 34/00* (2016.01)
(Continued)

(52) U.S. Cl.
CPC ........ *A61B 34/37* (2016.02); *A61B 17/07207* (2013.01); *A61B 34/71* (2016.02);
(Continued)

(58) Field of Classification Search
CPC ......... A61B 34/30; A61B 34/37; A61B 34/71; A61B 34/77; A61B 17/07207;
(Continued)

(56) References Cited

U.S. PATENT DOCUMENTS

| 6,132,368 | A | 10/2000 | Cooper |
| 6,206,903 | B1 | 3/2001 | Ramans |

(Continued)

FOREIGN PATENT DOCUMENTS

| CN | 107427329 | * 12/2017 | ............. A61B 34/30 |
| KR | 1020160141806 | * 12/2016 | ............. A61B 34/30 |

OTHER PUBLICATIONS

International Search Report and Written Opinion of the International Searching Authority issued in corresponding application PCT/IB2023/054310 mailed Aug. 17, 2023 (15 pages).

*Primary Examiner* — Linda J. Hodge
(74) *Attorney, Agent, or Firm* — Carter, DeLuca & Farrell, LLP

(57) ABSTRACT

A surgical robotic system includes a surgeon console configured to receive user input and a robotic arm configured to hold an instrument drive unit and an instrument coupled to the instrument drive unit. The instrument is controllable in response to the user input and includes an elongate shaft and an end effector coupled to the elongate shaft at a joint. The end effector is configured to pivot about at least one pivot axis relative to the elongate shaft. The instrument also includes a flexible drive rod configured to move longitudinally through the joint and to actuate at least one function of the end effector. The flexible drive rod is disposed off-axis relative to at least one pivot axis of the joint. The system also includes a controller configured to calculate a bend radius of the flexible drive rod during pivoting of the end effector; calculate a compensation distance based on the bend radius;

(Continued)

300 — Rotate end effector about pivot axis (e.g., pitch)

301 — Determine whether rotation affects the drive rod, i.e., whether joint is bent at specific pivot axis 302 — Determine angle of rotation about pivot axis 303 — Calculate bend radius of drive rod based on angle of rotation 304 — Calculate path length of drive rod using bend radius 306 — Set compensation distance based on path length 308 — Adjust actuation distance by compensation distance 310 — Instruct motor(s) to move firing rod by adjusted firing distance and command the instrument drive unit to advance the flexible drive rod by an actuation distance adjusted by the compensation distance.

20 Claims, 9 Drawing Sheets

(51) Int. Cl.

| | |
|---|---|
| *A61B 34/30* | (2016.01) |
| *A61B 34/37* | (2016.01) |
| *A61B 34/20* | (2016.01) |
| *A61B 90/00* | (2016.01) |

(52) U.S. Cl.
CPC .... *A61B 34/77* (2016.02); *A61B 2017/07257* (2013.01); *A61B 2017/07271* (2013.01); *A61B 2034/2059* (2016.02); *A61B 2034/302* (2016.02); *A61B 2090/067* (2016.02)

(58) Field of Classification Search
CPC ...... A61B 2034/2059; A61B 2090/067; A61B 2017/07257; A61B 2017/07271; A61B 2017/2927; A61B 17/285; A61B 17/295
USPC .......................................... 227/175.1–182.1
See application file for complete search history.

(56) References Cited

U.S. PATENT DOCUMENTS

| | | | |
|---|---|---|---|
| 6,246,200 | B1 | 6/2001 | Blumenkranz et al. |
| 6,312,435 | B1 | 11/2001 | Wallace et al. |
| 6,331,181 | B1 | 12/2001 | Tierney et al. |
| 6,394,998 | B1 | 5/2002 | Wallace et al. |
| 6,424,885 | B1 | 7/2002 | Niemeyer et al. |
| 6,441,577 | B2 | 8/2002 | Blumenkranz et al. |
| 6,459,926 | B1 | 10/2002 | Nowlin et al. |
| 6,491,691 | B1 | 12/2002 | Morley et al. |
| 6,491,701 | B2 | 12/2002 | Tierney et al. |
| 6,493,608 | B1 | 12/2002 | Niemeyer |
| 6,565,554 | B1 | 5/2003 | Niemeyer |
| 6,645,196 | B1 | 11/2003 | Nixon et al. |
| 6,659,939 | B2 | 12/2003 | Moll |
| 6,671,581 | B2 | 12/2003 | Niemeyer et al. |
| 6,676,684 | B1 | 1/2004 | Morley et al. |
| 6,685,698 | B2 | 2/2004 | Morley et al. |
| 6,699,235 | B2 | 3/2004 | Wallace et al. |
| 6,714,839 | B2 | 3/2004 | Salisbury, Jr. et al. |
| 6,716,233 | B1 | 4/2004 | Whitman |
| 6,728,599 | B2 | 4/2004 | Wang et al. |
| 6,746,443 | B1 | 6/2004 | Morley et al. |
| 6,766,204 | B2 | 7/2004 | Niemeyer et al. |
| 6,770,081 | B1 | 8/2004 | Cooper et al. |
| 6,772,053 | B2 | 8/2004 | Niemeyer |
| 6,783,524 | B2 | 8/2004 | Anderson et al. |
| 6,793,652 | B1 | 9/2004 | Whitman et al. |
| 6,793,653 | B2 | 9/2004 | Sanchez et al. |
| 6,799,065 | B1 | 9/2004 | Niemeyer |
| 6,837,883 | B2 | 1/2005 | Moll et al. |
| 6,839,612 | B2 | 1/2005 | Sanchez et al. |
| 6,840,938 | B1 | 1/2005 | Morley et al. |
| 6,843,403 | B2 | 1/2005 | Whitman |
| 6,846,309 | B2 | 1/2005 | Whitman et al. |
| 6,866,671 | B2 | 3/2005 | Tierney et al. |
| 6,871,117 | B2 | 3/2005 | Wang et al. |
| 6,879,880 | B2 | 4/2005 | Nowlin et al. |
| 6,899,705 | B2 | 5/2005 | Niemeyer |
| 6,902,560 | B1 | 6/2005 | Morley et al. |
| 6,936,042 | B2 | 8/2005 | Wallace et al. |
| 6,951,535 | B2 | 10/2005 | Ghodoussi et al. |
| 6,974,449 | B2 | 12/2005 | Niemeyer |
| 6,991,627 | B2 | 1/2006 | Madhani et al. |
| 6,994,708 | B2 | 2/2006 | Manzo |
| 7,048,745 | B2 | 5/2006 | Tierney et al. |
| 7,066,926 | B2 | 6/2006 | Wallace et al. |
| 7,118,582 | B1 | 10/2006 | Wang et al. |
| 7,125,403 | B2 | 10/2006 | Julian et al. |
| 7,155,315 | B2 | 12/2006 | Niemeyer et al. |
| 7,239,940 | B2 | 7/2007 | Wang et al. |
| 7,306,597 | B2 | 12/2007 | Manzo |
| 7,357,774 | B2 | 4/2008 | Cooper |
| 7,373,219 | B2 | 5/2008 | Nowlin et al. |
| 7,379,790 | B2 | 5/2008 | Toth et al. |
| 7,386,365 | B2 | 6/2008 | Nixon |
| 7,391,173 | B2 | 6/2008 | Schena |
| 7,398,707 | B2 | 7/2008 | Morley et al. |
| 7,413,565 | B2 | 8/2008 | Wang et al. |
| 7,453,227 | B2 | 11/2008 | Prisco et al. |
| 7,524,320 | B2 | 4/2009 | Tierney et al. |
| 7,574,250 | B2 | 8/2009 | Niemeyer |
| 7,594,912 | B2 | 9/2009 | Cooper et al. |
| 7,607,440 | B2 | 10/2009 | Coste-Maniere et al. |
| 7,666,191 | B2 | 2/2010 | Orban, III et al. |
| 7,682,357 | B2 | 3/2010 | Ghodoussi et al. |
| 7,689,320 | B2 | 3/2010 | Prisco et al. |
| 7,695,481 | B2 | 4/2010 | Wang et al. |
| 7,695,485 | B2 | 4/2010 | Whitman et al. |
| 7,699,855 | B2 | 4/2010 | Anderson et al. |
| 7,713,263 | B2 | 5/2010 | Niemeyer |
| 7,725,214 | B2 | 5/2010 | Diolaiti |
| 7,727,244 | B2 | 6/2010 | Orban, III et al. |
| 7,741,802 | B2 | 6/2010 | Prisco |
| 7,756,036 | B2 | 7/2010 | Druke et al. |
| 7,757,028 | B2 | 7/2010 | Druke et al. |
| 7,762,825 | B2 | 7/2010 | Burbank et al. |
| 7,778,733 | B2 | 8/2010 | Nowlin et al. |
| 7,803,151 | B2 | 9/2010 | Whitman |
| 7,806,891 | B2 | 10/2010 | Nowlin et al. |
| 7,819,859 | B2 | 10/2010 | Prisco et al. |
| 7,819,885 | B2 | 10/2010 | Cooper |
| 7,824,401 | B2 | 11/2010 | Manzo et al. |
| 7,835,823 | B2 | 11/2010 | Sillman et al. |
| 7,843,158 | B2 | 11/2010 | Prisco |
| 7,865,266 | B2 | 1/2011 | Moll et al. |
| 7,865,269 | B2 | 1/2011 | Prisco et al. |
| 7,886,743 | B2 | 2/2011 | Cooper et al. |
| 7,899,578 | B2 | 3/2011 | Prisco et al. |
| 7,907,166 | B2 | 3/2011 | Lamprecht et al. |
| 7,935,130 | B2 | 5/2011 | Williams |
| 7,963,913 | B2 | 6/2011 | Devengenzo et al. |
| 7,983,793 | B2 | 7/2011 | Toth et al. |
| 8,002,767 | B2 | 8/2011 | Sanchez |
| 8,004,229 | B2 | 8/2011 | Nowlin et al. |
| 8,012,170 | B2 | 9/2011 | Whitman et al. |
| 8,054,752 | B2 | 11/2011 | Druke et al. |
| 8,062,288 | B2 | 11/2011 | Cooper et al. |
| 8,079,950 | B2 | 12/2011 | Stern et al. |
| 8,100,133 | B2 | 1/2012 | Mintz et al. |
| 8,108,072 | B2 | 1/2012 | Zhao et al. |
| 8,120,301 | B2 | 2/2012 | Goldberg et al. |
| 8,142,447 | B2 | 3/2012 | Cooper et al. |
| 8,147,503 | B2 | 4/2012 | Zhao et al. |
| 8,151,661 | B2 | 4/2012 | Schena et al. |
| 8,155,479 | B2 | 4/2012 | Hoffman et al. |
| 8,182,469 | B2 | 5/2012 | Anderson et al. |
| 8,202,278 | B2 | 6/2012 | Orban, III et al. |
| 8,206,406 | B2 | 6/2012 | Orban, III |
| 8,210,413 | B2 | 7/2012 | Whitman et al. |
| 8,216,250 | B2 | 7/2012 | Orban, III et al. |
| 8,220,468 | B2 | 7/2012 | Cooper et al. |
| 8,256,319 | B2 | 9/2012 | Cooper et al. |
| 8,285,517 | B2 | 10/2012 | Sillman et al. |
| 8,315,720 | B2 | 11/2012 | Mohr et al. |
| 8,335,590 | B2 | 12/2012 | Costa et al. |
| 8,347,757 | B2 | 1/2013 | Duval |
| 8,374,723 | B2 | 2/2013 | Zhao et al. |
| 8,418,073 | B2 | 4/2013 | Mohr et al. |
| 8,419,717 | B2 | 4/2013 | Diolaiti et al. |
| 8,423,182 | B2 | 4/2013 | Robinson et al. |
| 8,452,447 | B2 | 5/2013 | Nixon |
| 8,454,585 | B2 | 6/2013 | Whitman |
| 8,499,992 | B2 | 8/2013 | Whitman et al. |
| 8,508,173 | B2 | 8/2013 | Goldberg et al. |

(56) References Cited

U.S. PATENT DOCUMENTS

| | | | |
|---|---|---|---|
| 8,528,440 | B2 | 9/2013 | Morley et al. |
| 8,529,582 | B2 | 9/2013 | Devengenzo et al. |
| 8,540,748 | B2 | 9/2013 | Murphy et al. |
| 8,551,116 | B2 | 10/2013 | Julian et al. |
| 8,562,594 | B2 | 10/2013 | Cooper et al. |
| 8,594,841 | B2 | 11/2013 | Zhao et al. |
| 8,597,182 | B2 | 12/2013 | Stein et al. |
| 8,597,280 | B2 | 12/2013 | Cooper et al. |
| 8,600,551 | B2 | 12/2013 | Itkowitz et al. |
| 8,608,773 | B2 | 12/2013 | Tierney et al. |
| 8,620,473 | B2 | 12/2013 | Diolaiti et al. |
| 8,624,537 | B2 | 1/2014 | Nowlin et al. |
| 8,634,957 | B2 | 1/2014 | Toth et al. |
| 8,638,056 | B2 | 1/2014 | Goldberg et al. |
| 8,638,057 | B2 | 1/2014 | Goldberg et al. |
| 8,644,988 | B2 | 2/2014 | Prisco et al. |
| 8,666,544 | B2 | 3/2014 | Moll et al. |
| 8,668,638 | B2 | 3/2014 | Donhowe et al. |
| 8,746,252 | B2 | 6/2014 | McGrogan et al. |
| 8,749,189 | B2 | 6/2014 | Nowlin et al. |
| 8,749,190 | B2 | 6/2014 | Nowlin et al. |
| 8,758,352 | B2 | 6/2014 | Cooper et al. |
| 8,761,930 | B2 | 6/2014 | Nixon |
| 8,768,516 | B2 | 7/2014 | Diolaiti et al. |
| 8,786,241 | B2 | 7/2014 | Nowlin et al. |
| 8,790,243 | B2 | 7/2014 | Cooper et al. |
| 8,808,164 | B2 | 8/2014 | Hoffman et al. |
| 8,816,628 | B2 | 8/2014 | Nowlin et al. |
| 8,821,480 | B2 | 9/2014 | Burbank |
| 8,823,308 | B2 | 9/2014 | Nowlin et al. |
| 8,827,989 | B2 | 9/2014 | Niemeyer |
| 8,838,270 | B2 | 9/2014 | Druke et al. |
| 8,852,174 | B2 | 10/2014 | Burbank |
| 8,858,547 | B2 | 10/2014 | Brogna |
| 8,862,268 | B2 | 10/2014 | Robinson et al. |
| 8,864,751 | B2 | 10/2014 | Prisco et al. |
| 8,864,752 | B2 | 10/2014 | Diolaiti et al. |
| 8,903,546 | B2 | 12/2014 | Diolaiti et al. |
| 8,903,549 | B2 | 12/2014 | Itkowitz et al. |
| 8,911,428 | B2 | 12/2014 | Cooper et al. |
| 8,912,746 | B2 | 12/2014 | Reid et al. |
| 8,944,070 | B2 | 2/2015 | Guthart |
| 8,989,903 | B2 | 3/2015 | Weir et al. |
| 9,002,518 | B2 | 4/2015 | Manzo |
| 9,014,856 | B2 | 4/2015 | Manzo et al. |
| 9,016,540 | B2 | 4/2015 | Whitman et al. |
| 9,019,345 | B2 | 4/2015 | O'Grady et al. |
| 9,043,027 | B2 | 5/2015 | Durant et al. |
| 9,050,120 | B2 | 6/2015 | Swarup et al. |
| 9,055,961 | B2 | 6/2015 | Manzo et al. |
| 9,060,770 | B2 | 6/2015 | Shelton, IV et al. |
| 9,068,628 | B2 | 6/2015 | Solomon et al. |
| 9,078,684 | B2 | 7/2015 | Williams |
| 9,084,623 | B2 | 7/2015 | Gomez et al. |
| 9,095,362 | B2 | 8/2015 | Dachs, II et al. |
| 9,096,033 | B2 | 8/2015 | Holop et al. |
| 9,101,381 | B2 | 8/2015 | Burbank et al. |
| 9,113,877 | B1 | 8/2015 | Whitman et al. |
| 9,138,284 | B2 | 9/2015 | Krom et al. |
| 9,144,456 | B2 | 9/2015 | Rosa et al. |
| 9,198,730 | B2 | 12/2015 | Prisco et al. |
| 9,204,923 | B2 | 12/2015 | Manzo et al. |
| 9,226,648 | B2 | 1/2016 | Saadat et al. |
| 9,226,750 | B2 | 1/2016 | Weir et al. |
| 9,226,761 | B2 | 1/2016 | Burbank |
| 9,232,984 | B2 | 1/2016 | Guthart et al. |
| 9,241,766 | B2 | 1/2016 | Duque et al. |
| 9,241,767 | B2 | 1/2016 | Prisco et al. |
| 9,241,769 | B2 | 1/2016 | Larkin et al. |
| 9,259,275 | B2 | 2/2016 | Burbank |
| 9,259,277 | B2 | 2/2016 | Rogers et al. |
| 9,259,281 | B2 | 2/2016 | Griffiths et al. |
| 9,259,282 | B2 | 2/2016 | Azizian et al. |
| 9,261,172 | B2 | 2/2016 | Solomon et al. |
| 9,265,567 | B2 | 2/2016 | Orban, III et al. |
| 9,265,584 | B2 | 2/2016 | Itkowitz et al. |
| 9,283,049 | B2 | 3/2016 | Diolaiti et al. |
| 9,301,811 | B2 | 4/2016 | Goldberg et al. |
| 9,314,307 | B2 | 4/2016 | Richmond et al. |
| 9,317,651 | B2 | 4/2016 | Nixon |
| 9,345,546 | B2 | 5/2016 | Toth et al. |
| 9,393,017 | B2 | 7/2016 | Flanagan et al. |
| 9,402,689 | B2 | 8/2016 | Prisco et al. |
| 9,417,621 | B2 | 8/2016 | Diolaiti |
| 9,424,303 | B2 | 8/2016 | Hoffman et al. |
| 9,433,418 | B2 | 9/2016 | Whitman et al. |
| 9,446,517 | B2 | 9/2016 | Burns et al. |
| 9,452,020 | B2 | 9/2016 | Griffiths et al. |
| 9,474,569 | B2 | 10/2016 | Manzo et al. |
| 9,480,533 | B2 | 11/2016 | Devengenzo et al. |
| 9,503,713 | B2 | 11/2016 | Zhao et al. |
| 9,550,300 | B2 | 1/2017 | Danitz et al. |
| 9,554,859 | B2 | 1/2017 | Nowlin et al. |
| 9,566,124 | B2 | 2/2017 | Prisco et al. |
| 9,579,164 | B2 | 2/2017 | Itkowitz et al. |
| 9,585,641 | B2 | 3/2017 | Cooper et al. |
| 9,615,883 | B2 | 4/2017 | Schena et al. |
| 9,623,563 | B2 | 4/2017 | Nixon |
| 9,623,902 | B2 | 4/2017 | Griffiths et al. |
| 9,629,520 | B2 | 4/2017 | Diolaiti |
| 9,662,177 | B2 | 5/2017 | Weir et al. |
| 9,664,262 | B2 | 5/2017 | Donlon et al. |
| 9,675,354 | B2 | 6/2017 | Weir et al. |
| 9,687,312 | B2 | 6/2017 | Dachs, II et al. |
| 9,700,334 | B2 | 7/2017 | Hinman et al. |
| 9,718,190 | B2 | 8/2017 | Larkin et al. |
| 9,730,719 | B2 | 8/2017 | Brisson et al. |
| 9,737,199 | B2 | 8/2017 | Pistor et al. |
| 9,795,446 | B2 | 10/2017 | DiMaio et al. |
| 9,797,484 | B2 | 10/2017 | Solomon et al. |
| 9,801,690 | B2 | 10/2017 | Larkin et al. |
| 9,814,530 | B2 | 11/2017 | Weir et al. |
| 9,814,536 | B2 | 11/2017 | Goldberg et al. |
| 9,814,537 | B2 | 11/2017 | Itkowitz et al. |
| 9,820,823 | B2 | 11/2017 | Richmond et al. |
| 9,827,059 | B2 | 11/2017 | Robinson et al. |
| 9,830,371 | B2 | 11/2017 | Hoffman et al. |
| 9,839,481 | B2 | 12/2017 | Blumenkranz et al. |
| 9,839,487 | B2 | 12/2017 | Dachs, II |
| 9,844,374 | B2 | 12/2017 | Lytle, IV et al. |
| 9,850,994 | B2 | 12/2017 | Schena |
| 9,855,102 | B2 | 1/2018 | Blumenkranz |
| 9,855,107 | B2 | 1/2018 | Labonville et al. |
| 9,872,737 | B2 | 1/2018 | Nixon |
| 9,877,718 | B2 | 1/2018 | Weir et al. |
| 9,883,920 | B2 | 2/2018 | Blumenkranz |
| 9,888,974 | B2 | 2/2018 | Niemeyer |
| 9,895,813 | B2 | 2/2018 | Blumenkranz et al. |
| 9,901,408 | B2 | 2/2018 | Larkin |
| 9,918,800 | B2 | 3/2018 | Itkowitz et al. |
| 9,943,375 | B2 | 4/2018 | Blumenkranz et al. |
| 9,948,852 | B2 | 4/2018 | Lilagan et al. |
| 9,949,798 | B2 | 4/2018 | Weir |
| 9,949,802 | B2 | 4/2018 | Cooper |
| 9,952,107 | B2 | 4/2018 | Blumenkranz et al. |
| 9,956,044 | B2 | 5/2018 | Gomez et al. |
| 9,980,778 | B2 | 5/2018 | Ohline et al. |
| 10,008,017 | B2 | 6/2018 | Itkowitz et al. |
| 10,028,793 | B2 | 7/2018 | Griffiths et al. |
| 10,033,308 | B2 | 7/2018 | Chaghajerdi et al. |
| 10,034,719 | B2 | 7/2018 | Richmond et al. |
| 10,052,167 | B2 | 8/2018 | Au et al. |
| 10,085,811 | B2 | 10/2018 | Weir et al. |
| 10,092,165 | B2 | 10/2018 | Power |
| 10,092,344 | B2 | 10/2018 | Mohr et al. |
| 10,123,844 | B2 | 11/2018 | Nowlin |
| 10,188,471 | B2 | 1/2019 | Brisson |
| 10,201,390 | B2 | 2/2019 | Swarup et al. |
| 10,213,202 | B2 | 2/2019 | Flanagan et al. |
| 10,258,416 | B2 | 4/2019 | Mintz et al. |
| 10,278,782 | B2 | 5/2019 | Jarc et al. |
| 10,278,783 | B2 | 5/2019 | Itkowitz et al. |
| 10,282,881 | B2 | 5/2019 | Itkowitz et al. |
| 10,335,242 | B2 | 7/2019 | Devengenzo et al. |

(56)  References Cited

U.S. PATENT DOCUMENTS

| | | | |
|---|---|---|---|
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 11,376,002 B2 | 7/2022 | Shelton, IV et al. |
| 11,376,098 B2 | 7/2022 | Shelton, IV et al. |
| 11,381,759 B2 | 7/2022 | Zhao et al. |
| 11,382,621 B2 | 7/2022 | Scheib et al. |
| 11,382,624 B2 | 7/2022 | Harris et al. |
| 11,382,625 B2 | 7/2022 | Huitema et al. |
| 11,382,626 B2 | 7/2022 | Shelton, IV et al. |
| 11,382,627 B2 | 7/2022 | Huitema et al. |
| 11,382,638 B2 | 7/2022 | Harris et al. |
| 11,382,644 B2 | 7/2022 | Schoettgen et al. |
| 11,389,160 B2 | 7/2022 | Shelton, IV et al. |
| 11,389,255 B2 | 7/2022 | DiMaio et al. |
| 11,399,906 B2 | 8/2022 | Shelton, IV et al. |
| 11,406,379 B2 | 8/2022 | Hess et al. |
| 11,410,259 B2 | 8/2022 | Harris et al. |
| 11,419,630 B2 | 8/2022 | Yates et al. |
| 11,424,027 B2 | 8/2022 | Shelton, IV |
| 11,432,888 B2 | 9/2022 | Diolaiti et al. |
| 11,432,893 B2 | 9/2022 | Itkowitz et al. |
| 11,432,895 B2 | 9/2022 | Loh et al. |
| 11,439,390 B2 | 9/2022 | Patel et al. |
| 11,439,391 B2 | 9/2022 | Bruns et al. |
| 11,468,791 B2 | 10/2022 | Jarc et al. |
| 11,471,155 B2 | 10/2022 | Shelton, IV et al. |
| 11,471,221 B2 | 10/2022 | Zhao et al. |
| 11,478,308 B2 | 10/2022 | Hoffman et al. |
| 11,490,977 B2 | 11/2022 | Schena et al. |
| 11,497,499 B2 | 11/2022 | Shelton, IV et al. |
| 11,504,119 B2 | 11/2022 | Shelton, IV et al. |
| 11,504,124 B2 | 11/2022 | Patel et al. |
| 11,510,743 B2 | 11/2022 | Shelton, IV et al. |
| 11,517,312 B2 | 12/2022 | Wixey |
| 11,517,325 B2 | 12/2022 | Shelton, IV et al. |
| 11,518,048 B2 | 12/2022 | Saraliev et al. |
| 12,161,323 B2 * | 12/2024 | Bakos .................. A61B 17/072 |
| 2010/0030029 A1 | 2/2010 | Markham |
| 2012/0298719 A1 | 11/2012 | Shelton, IV et al. |
| 2014/0263539 A1 | 9/2014 | Leimbach et al. |
| 2016/0174977 A1 * | 6/2016 | Lytle, IV ............. A61B 17/068 |
| | | 227/180.1 |
| 2016/0346513 A1 * | 12/2016 | Swaney ............ A61M 25/0138 |
| 2017/0224335 A1 | 8/2017 | Weaner et al. |
| 2019/0059889 A1 | 2/2019 | Shelton, IV et al. |
| 2019/0365487 A1 * | 12/2019 | D'Amelio .............. A61B 34/70 |

* cited by examiner

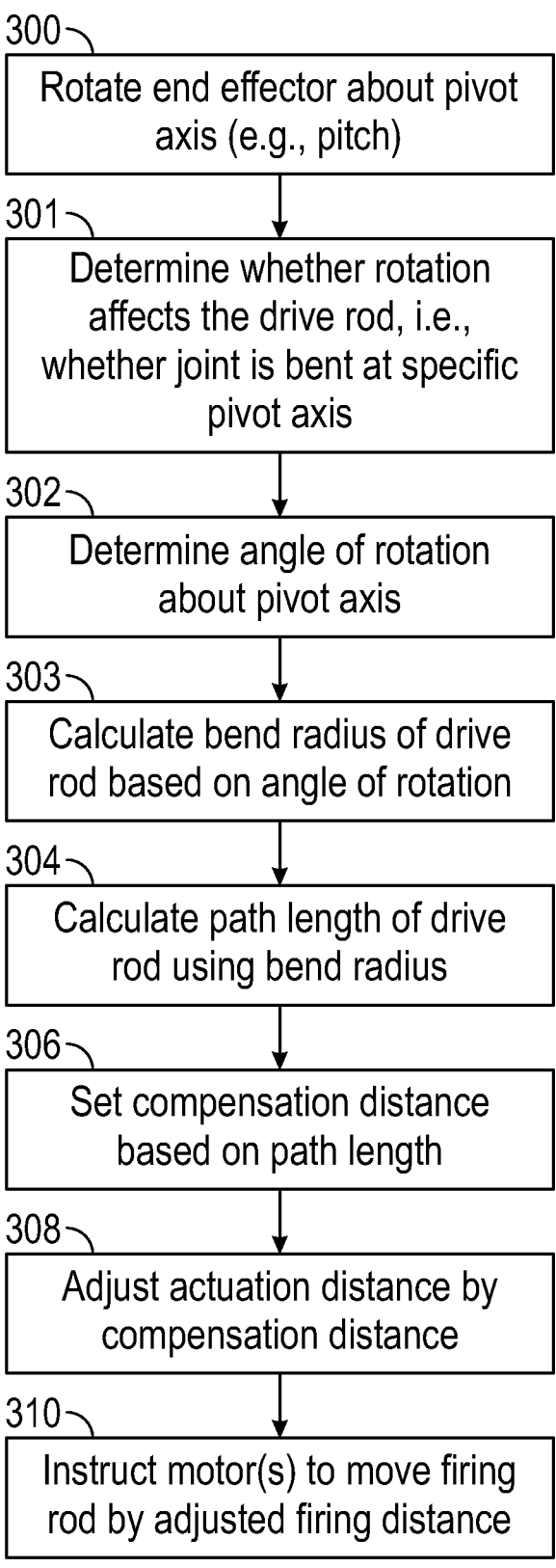

300 — Rotate end effector about pivot axis (e.g., pitch)

301 — Determine whether rotation affects the drive rod, i.e., whether joint is bent at specific pivot axis 302 — Determine angle of rotation about pivot axis 303 — Calculate bend radius of drive rod based on angle of rotation 304 — Calculate path length of drive rod using bend radius 306 — Set compensation distance based on path length 308 — Adjust actuation distance by compensation distance 310 — Instruct motor(s) to move firing rod by adjusted firing distance

FIG. 9

SYSTEM AND METHOD FOR COMPENSATION FOR AN OFF-AXIS PUSH-PULL DRIVE ROD IN A ROBOTICALLY ASSISTED SURGICAL INSTRUMENT

BACKGROUND

Surgical robotic systems may include a surgeon console controlling one or more surgical robotic arms, each including a surgical instrument having an end effector (e.g., forceps or grasping instrument). In operation, the robotic arm is moved to a position over a patient and the surgical instrument is guided into a small incision via a surgical access port or a natural orifice of a patient to position the end effector at a work site within the patient's body. The surgeon console includes hand controllers which translate user input into movement of the surgical instrument and/or end effector.

The surgical instrument may be a surgical stapler having an end effector configured to clamp, fasten, and cut tissue. A drive mechanism may be advanced to approximate a pair of jaws of the end effector while simultaneously ejecting fasteners and cutting tissue. After completing the procedure, the jaws of the surgical stapler are opened to release tissue by reversing the drive mechanism.

Wristed surgical staplers (or other instruments) may also incorporate push-pull rods to actuate various end effector components, e.g., jaw opening, knife advancement, staple ejection, etc. However, advancement of the push-pull rod while the surgical instrument is pivoted or articulated may result in unintended movement of the end effector. Thus, there is a need for compensation for unintended movement of the end effector during actuation of the push-pull rod.

SUMMARY

Surgical wristed end effectors utilizing push-pull drive rods may position the drive rod in a variety of locations. In embodiments, the drive rod may be disposed along a neutral axis of a wrist joint. As the end effector is pivoted about the wrist joint, the path of the drive rod does not change, and the operation of the drive rod is not affected by the pitch and/or yaw of the wristed end effector. However, in other embodiments, the push-pull drive rod may be placed off axis, i.e., away from the neutral axis, due to a variety of design configurations, e.g., routing of other components through the end effector. Thus, if the drive rod is not disposed along the neutral axis of the wrist joint, then the path of the drive rod would be affected. In other words, pitch and/or yaw articulation of end effector would result in shifting the output of the drive rod, i.e., as the end effector is pivoted, the drive rod is moved longitudinally. As a result, such shifting may cause unintended movement of the drive rod during articulation of the end effector.

The present disclosure provides for a software algorithm which may be implemented as software instructions executable by a controller of a surgical robotic system or a powered surgical instrument. In embodiments, a controller of an instrument drive unit includes one or more motors controlling a wristed end effector. The software algorithm is configured to adjust a longitudinal position of an off-axis drive rod based on pitch and/or yaw degree of freedom of a surgical end effector. As used herein the term off-axis denotes a longitudinal axis that is off-center either in a horizontal axis, i.e., yaw, or a vertical axis, i.e., pitch. A flexible push-pull drive rod that is disposed along a neutral axis is bent at a wrist joint while the end effector is articulated. However, a drive rod that is disposed off-axis is bent further than a neutral axis drive rod due to additional offset distance from the center of the bending radius of the wrist joint. The effect of the offset results in lengthening of the travel distance for the drive rod.

The algorithm is configured to calculate a compensation distance based on a change in a path length of the drive rod. The path length may be determined by measuring the bending radius of the drive rod and multiplying by $2\pi$, i.e., circumference formula, since the push-pull movement is following the circumference of a theoretical circle. The path length depends on a type of a wrist joint that connects the end effector to a shaft of the surgical instrument. Thus, where a single pivot pin is used to form a wrist joint, the bending radius is substantially equal to the offset distance of the drive rod longitudinal from a neutral axis. In embodiments, where multi-component wrist joint is used, e.g., stacked vertebrae, then the bending radius is variable and may be calculated based on the articulation angle. The pitch and/or yaw angle may be determined using motor position. In embodiments, any suitable articulation angle sensors may also be used. The angle measurements are provided to the controller which then determines the radius based on the articulation angle. Once the path length is calculated, the compensation distance is set to be equal to a value of the calculated path length and the instrument drive unit controller may then instruct one or more motors to adjust the drive rod by the compensation distance.

According to one embodiment of the present disclosure, a surgical robotic system is disclosed. The surgical robotic system includes a surgeon console configured to receive user input, and a robotic arm configured to hold an instrument drive unit and an instrument coupled to the instrument drive unit. The instrument is controllable in response to the user input and includes an elongate shaft and an end effector coupled to the elongate shaft at a joint. The end effector is configured to pivot about at least one pivot axis relative to the elongate shaft. The instrument also includes a flexible drive rod configured to move longitudinally through the joint and to actuate at least one function of the end effector. The flexible drive rod is disposed off-axis relative to at least one pivot axis of the joint. The system also includes a controller configured to calculate a bend radius of the flexible drive rod during pivoting of the end effector; calculate a compensation distance based on the bend radius; and command the instrument drive unit to advance the flexible drive rod by an actuation distance adjusted by the compensation distance.

Implementations of the above embodiment may include one or more of the following features. According to one aspect of the above embodiment, the controller may be further configured to calculate the bend radius based on an angle of the pivoting of the end effector. The instrument drive unit may be configured to measure the angle of the pivoting of the end effector. The controller may be further configured to receive the user input, which may include a command for pivoting the end effector and to determine whether the command lengthens the actuation distance of the flexible drive rod. The end effector may be a surgical stapler, which may include an anvil and a cartridge having a plurality of staples. During longitudinal advancement, the flexible drive rod may be configured to approximate the anvil relative to the cartridge and/or to eject the plurality of staples from the cartridge.

According to another embodiment of the present disclosure, a surgical robotic system is disclosed. The surgical robotic system includes an instrument drive unit and an instrument coupled to the instrument drive unit. The instrument includes an elongate shaft and an end effector coupled to the elongate shaft at a joint. The end effector is configured to pivot about at least one pivot axis relative to the elongate shaft. The instrument also includes a flexible drive rod configured to move longitudinally through the joint and to actuate at least one function of the end effector. The flexible drive rod is disposed off-axis relative to at least one pivot axis of the joint. The system also includes a controller configured to: calculate a bend radius of the flexible drive rod during pivoting of the end effector; calculate a compensation distance based on the bend radius; and command the instrument drive unit to advance the flexible drive rod by an actuation distance adjusted by the compensation distance.

Implementations of the above embodiment may include one or more of the following features. According to one aspect of the above embodiment, the controller may be further configured to calculate the bend radius based on an angle of the pivoting of the end effector. The instrument drive unit may be configured to measure the angle of the pivoting of the end effector. The controller may be further configured to receive a command for pivoting the end effector and to determine whether the command lengthens the actuation distance of the flexible drive rod. The end effector may be a surgical stapler, which may include an anvil and a cartridge having a plurality of staples. During longitudinal advancement, the flexible drive rod may be configured to approximate the anvil relative to the cartridge and/or to eject the plurality of staples from the cartridge.

According to a further embodiment of the present disclosure, a method for controlling a surgical robotic system is disclosed. The method includes pivoting an end effector coupled to an elongate shaft of an instrument at a joint about at least one pivot axis relative to the elongate shaft. The method also includes calculating a bend radius of a flexible drive rod during pivoting of the end effector. The flexible drive rod is configured to move longitudinally through the joint and to actuate at least one function of the end effector. The flexible drive rod is disposed off-axis relative to at least one pivot axis of the joint. The method also includes calculating a compensation distance based on the bend radius. The method also includes commanding an instrument drive unit coupled to the instrument to advance the flexible drive rod by an actuation distance adjusted by the compensation distance.

Implementations of the above embodiment may include one or more of the following features. According to one aspect of the above embodiment, the method may also include calculating the bend radius based on an angle of the pivoting of the end effector. The method may further include measuring the angle of the pivoting of the end effector. The method may additionally include receiving a command for pivoting the end effector and determining whether the command lengthens the actuation distance of the flexible drive rod. The end effector may be a surgical stapler including an anvil and a cartridge having a plurality of staples. The method may also include advancing the flexible drive rod to approximate the anvil relative to the cartridge and to eject the plurality of staples from the cartridge.

BRIEF DESCRIPTION OF THE DRAWINGS

Various embodiments of the present disclosure are described herein with reference to the drawings wherein:

FIG. 9 is a flow chart of a method for compensation for an off-axis push-pull drive rod of the surgical instrument of FIG. 6.

DETAILED DESCRIPTION

Figure 1:
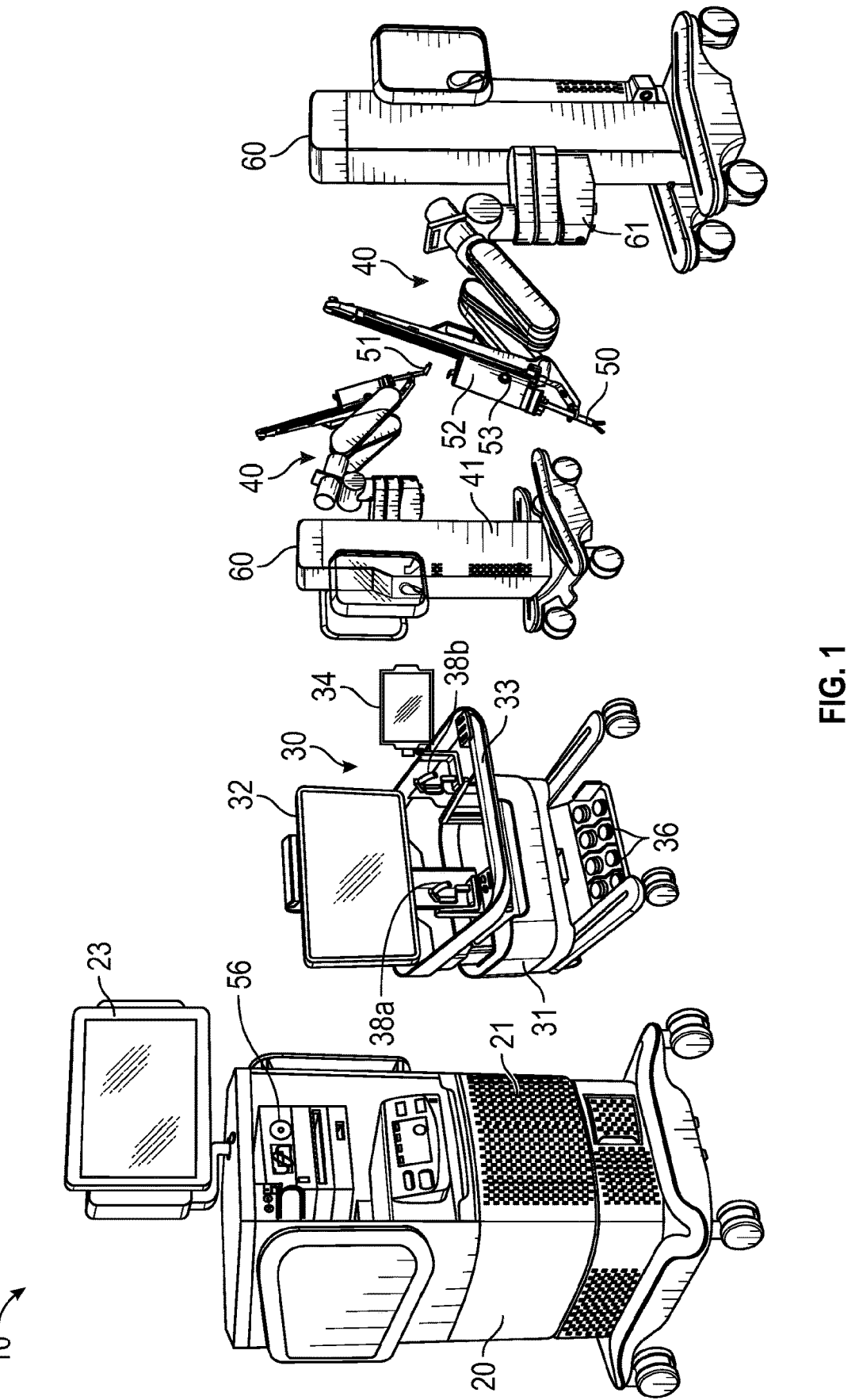
FIG. 1 is a schematic illustration of a surgical robotic system including a control tower, a console, and one or more surgical robotic arms each disposed on a mobile cart according to an embodiment of the present disclosure.

Embodiments of the presently disclosed surgical robotic system are described in detail with reference to the drawings, in which like reference numerals designate identical or corresponding elements in each of the several views. As used herein the term "proximal" refers to the portion of the surgical robotic system and/or the surgical instrument coupled thereto that is closer to a base of a robot, while the term "distal" refers to the portion that is farther from the base of the robot.

As will be described in detail below, the present disclosure is directed to a surgical robotic system, which includes a surgeon console, a control tower, and one or more mobile carts having a surgical robotic arm coupled to a setup arm. The surgeon console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which would, in turn, move the robotic arm in response to the movement command.

With reference to FIG. 1, a powered surgical system, such as a surgical robotic system 10 includes a control tower 20, which is connected to all of the components of the surgical robotic system 10 including a surgeon console 30 and one or more movable carts 60. Each of the movable carts 60 includes a robotic arm 40 having a surgical instrument 50 removably coupled thereto. The robotic arms 40 also couple to the movable carts 60. The robotic system 10 may include any number of movable carts 60 and/or robotic arms 40.

The surgical instrument 50 is configured for use during minimally invasive surgical procedures. In embodiments, the surgical instrument 50 may be configured for open surgical procedures. In embodiments, the surgical instrument 50 may be an endoscope, such as an endoscopic camera 51, configured to provide a video feed for the user. In further embodiments, the surgical instrument 50 may be an electrosurgical forceps configured to seal tissue by compressing tissue between jaw members and applying electrosurgical current thereto. In yet further embodiments, the surgical instrument 50 may be a surgical stapler including a pair of jaws configured to grasp and clamp tissue while deploying a plurality of tissue fasteners, e.g., staples, and cutting stapled tissue.

One of the robotic arms 40 may include the endoscopic camera 51 configured to capture video of the surgical site. The endoscopic camera 51 may be a stereoscopic endoscope configured to capture two side-by-side (i.e., left and right) images of the surgical site to produce a video stream of the surgical scene. The endoscopic camera 51 is coupled to a video processing device 56, which may be disposed within the control tower 20. The video processing device 56 may be any computing device as described below configured to receive the video feed from the endoscopic camera 51 and output the processed video stream.

The surgeon console 30 includes a first display 32, which displays a video feed of the surgical site provided by camera 51 of the surgical instrument 50 disposed on the robotic arm 40, and a second display 34, which displays a user interface for controlling the surgical robotic system 10. The first and second displays 32 and 34 are touchscreens allowing for displaying various graphical user inputs.

The surgeon console 30 also includes a plurality of user interface devices, such as foot pedals 36 and a pair of handle controllers 38a and 38b which are used by a user to remotely control robotic arms 40. The surgeon console further includes an armrest 33 used to support clinician's arms while operating the handle controllers 38a and 38b.

The control tower 20 includes a display 23, which may be a touchscreen, and outputs on the graphical user interfaces (GUIs). The control tower 20 also acts as an interface between the surgeon console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgeon console 30, in such a way that robotic arms 40 and the surgical instrument 50 execute a desired movement sequence in response to input from the foot pedals 36 and the handle controllers 38a and 38b.

Each of the control tower 20, the surgeon console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area network, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-1203 standard for wireless personal area networks (WPANs)).

The computers 21, 31, 41 may include any suitable processor (not shown) operably connected to a memory (not shown), which may include one or more of volatile, nonvolatile, magnetic, optical, or electrical media, such as read-only memory (ROM), random access memory (RAM), electrically-erasable programmable ROM (EEPROM), nonvolatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
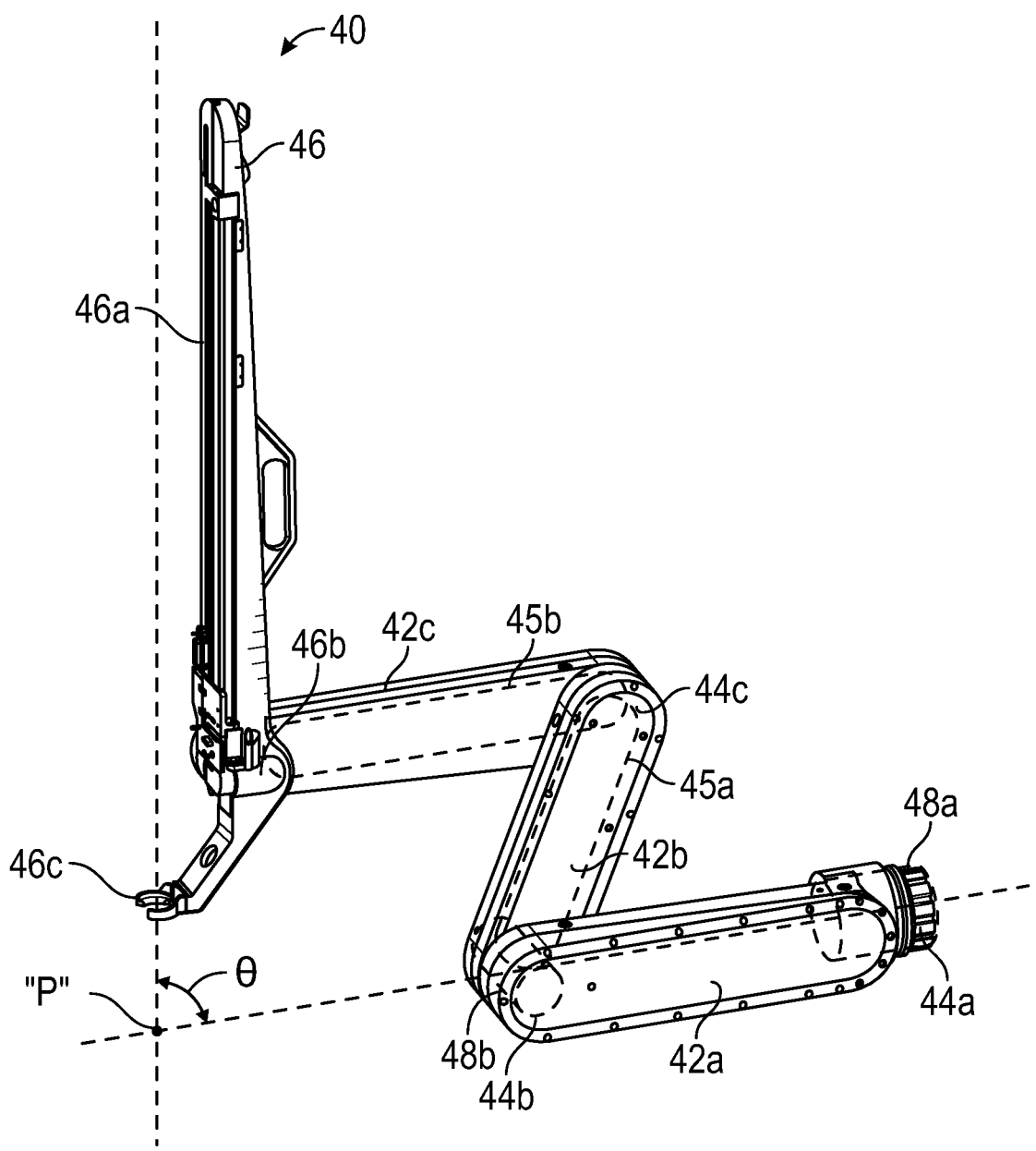
FIG. 2 is a perspective view of a surgical robotic arm of the surgical robotic system of FIG. 1 according to an embodiment of the present disclosure.
Figure 3:
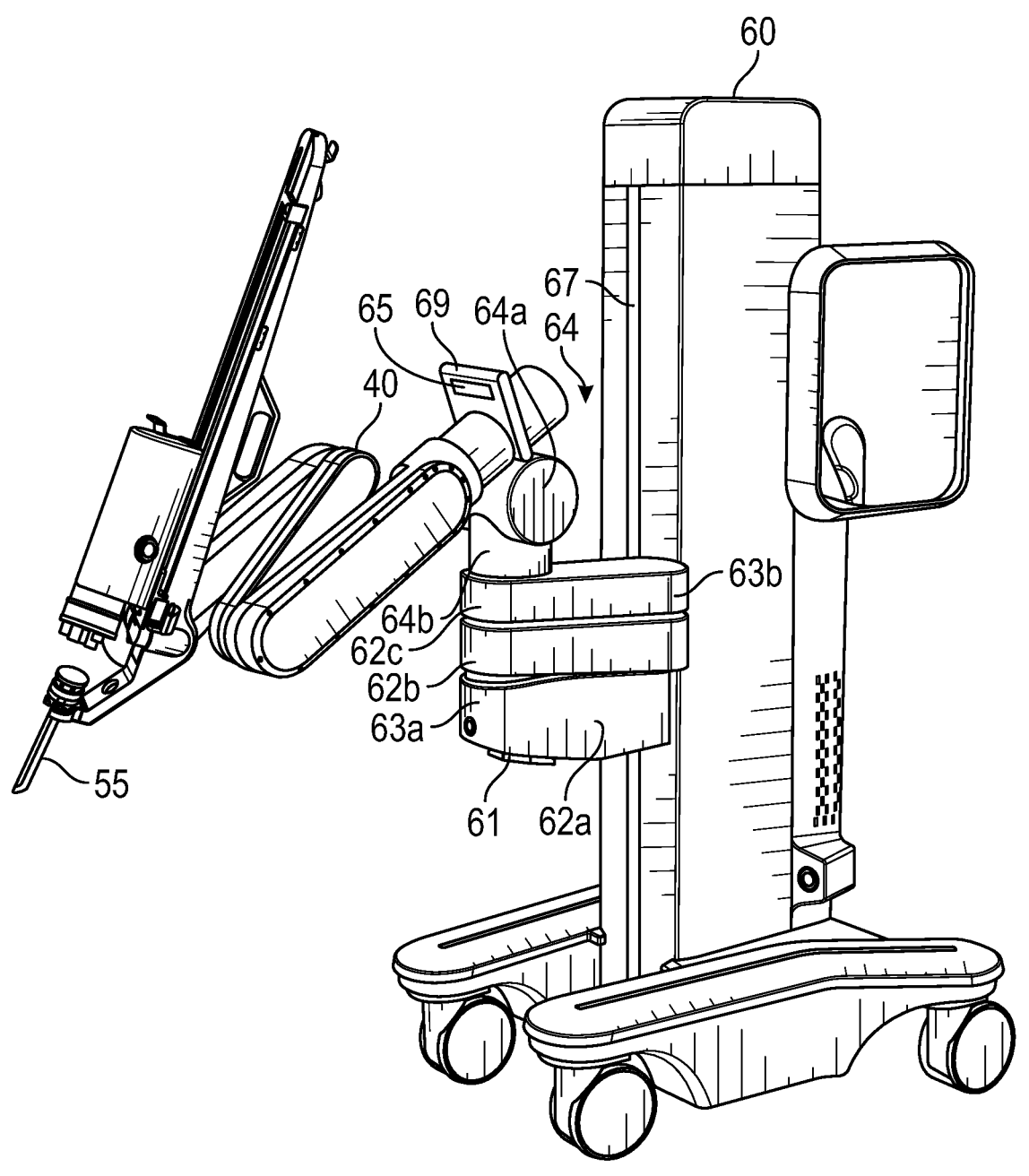
FIG. 3 is a perspective view of a mobile cart having a setup arm with the surgical robotic arm of the surgical robotic system of FIG. 1 according to an embodiment of the present disclosure.

With reference to FIG. 2, each of the robotic arms 40 may include a plurality of links 42a, 42b, 42c, which are interconnected at joints 44a, 44b, 44c, respectively. Other configurations of links and joints may be utilized as known by those skilled in the art. The joint 44a is configured to secure the robotic arm 40 to the mobile cart 60 and defines a first longitudinal axis. With reference to FIG. 3, the mobile cart 60 includes a lift 67 and a setup arm 61, which provides a base for mounting of the robotic arm 40. The lift 67 allows for vertical movement of the setup arm 61. The mobile cart 60 also includes a display 69 for displaying information pertaining to the robotic arm 40. In embodiments, the robotic arm 40 may include any type and/or number of joints.

The setup arm 61 includes a first link 62a, a second link 62b, and a third link 62c, which provide for lateral maneuverability of the robotic arm 40. The links 62a, 62b, 62c are interconnected at joints 63a and 63b, each of which may include an actuator (not shown) for rotating the links 62b and 62b relative to each other and the link 62c. In particular, the links 62a, 62b, 62c are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 61 includes controls 65 for adjusting movement of the links 62a, 62b, 62c as well as the lift 67. In embodiments, the setup arm 61 may include any type and/or number of joints.

The third link 62c may include a rotatable base 64 having two degrees of freedom. In particular, the rotatable base 64 includes a first actuator 64a and a second actuator 64b. The first actuator 64a is rotatable about a first stationary arm axis which is perpendicular to a plane defined by the third link 62c and the second actuator 64b is rotatable about a second stationary arm axis which is transverse to the first stationary arm axis. The first and second actuators 64a and 64b allow for full three-dimensional orientation of the robotic arm 40.

The actuator 48b of the joint 44b is coupled to the joint 44c via the belt 45a, and the joint 44c is in turn coupled to the joint 46b via the belt 45b. Joint 44c may include a transfer case coupling the belts 45a and 45b, such that the actuator 48b is configured to rotate each of the links 42b, 42c and a holder 46 relative to each other. More specifically, links 42b, 42c, and the holder 46 are passively coupled to the actuator 48b which enforces rotation about a pivot point "P" which lies at an intersection of the first axis defined by the link 42a and the second axis defined by the holder 46. In other words, the pivot point "P" is a remote center of motion (RCM) for the robotic arm 40. Thus, the actuator 48b controls the angle θ between the first and second axes allowing for orientation of the surgical instrument 50. Due to the interlinking of the links 42a, 42b, 42c, and the holder 46 via the belts 45a and 45b, the angles between the links 42a, 42b, 42c, and the holder 46 are also adjusted in order to achieve the desired angle θ. In embodiments, some or all of the joints 44a, 44b, 44c may include an actuator to obviate the need for mechanical linkages.

The joints 44a and 44b include an actuator 48a and 48b configured to drive the joints 44a, 44b, 44c relative to each other through a series of belts 45a and 45b or other mechanical linkages such as a drive rod, a cable, or a lever and the like. In particular, the actuator 48a is configured to rotate the robotic arm 40 about a longitudinal axis defined by the link 42a.

With reference to FIG. 2, the holder 46 defines a second longitudinal axis and configured to receive an instrument drive unit (IDU) 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components (e.g., end effector) of the surgical instrument 50. The holder 46 includes a sliding mechanism 46a, which is configured to move the IDU 52 along the second longitudinal axis defined by the holder 46. The holder 46 also includes a joint 46b, which rotates the holder 46 relative to the link 42c. During endoscopic procedures, the instrument 50 may be inserted through an endoscopic access port 55 (FIG. 3) held by the holder 46. The holder 46 also includes a port latch 46c for securing the access port 55 to the holder 46 (FIG. 2).

The robotic arm 40 also includes a plurality of manual override buttons 53 (FIG. 1) disposed on the IDU 52 and the setup arm 61, which may be used in a manual mode. The user may press one or more of the buttons 53 to move the component associated with the button 53.

Figure 4:
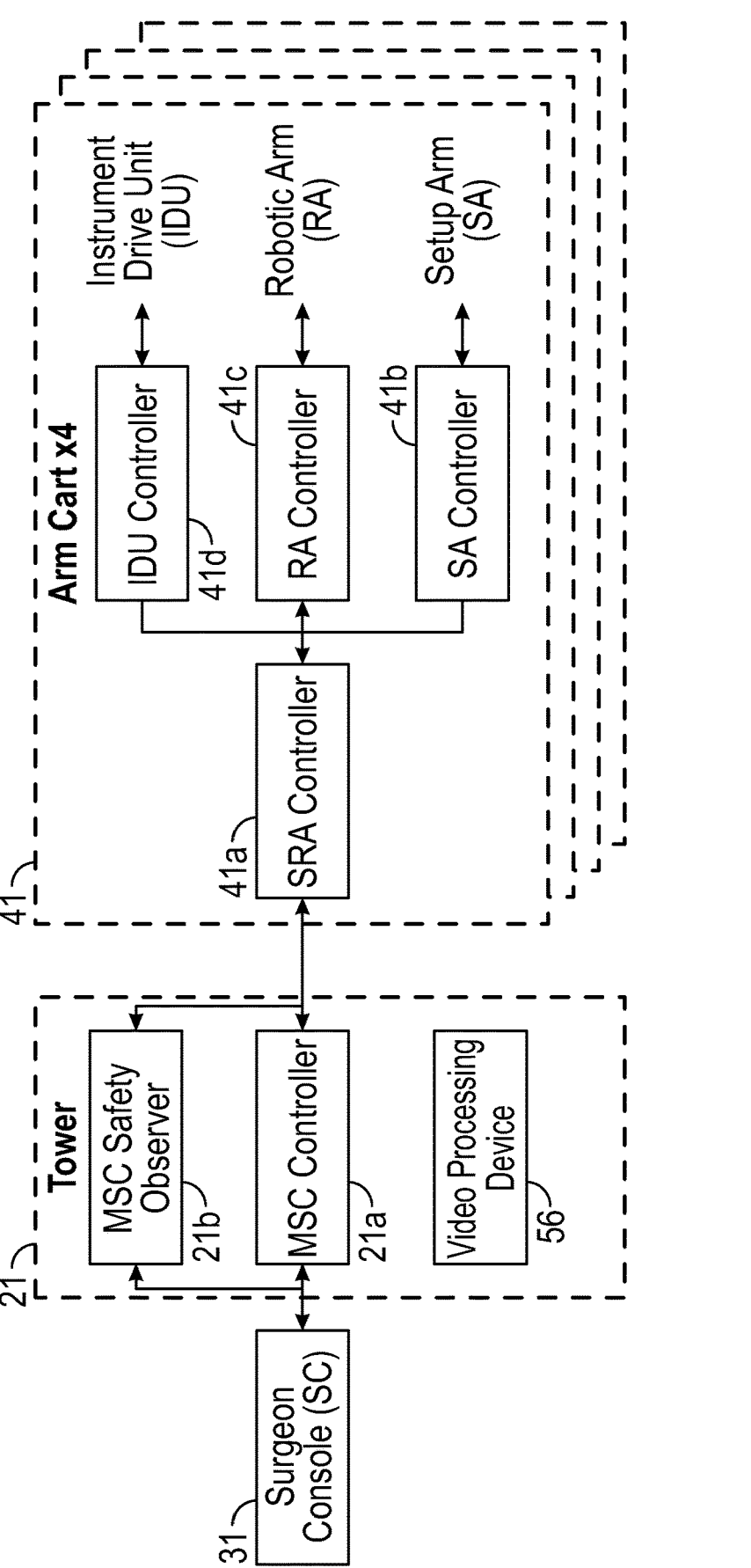
FIG. 4 is a schematic diagram of a computer architecture of the surgical robotic system of FIG. 1 according to an embodiment of the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21a and safety observer 21b. The controller 21a receives data from the computer 31 of the surgeon console 30 about the current position and/or orientation of the handle controllers 38a and 38b and the state of the foot pedals 36 and other buttons. The controller 21a processes these input positions to determine desired drive commands for each joint of the robotic arm 40 and/or the IDU 52 and communicates these to the computer 41 of the robotic arm 40. The controller 21a also receives the actual joint angles measured by encoders of the actuators 48a and 48b and uses this information to determine force feedback commands that are transmitted back to the computer 31 of the surgeon console 30 to provide haptic feedback through the handle controllers 38a and 38b. The safety observer 21b performs validity checks on the data going into and out of the controller 21a and notifies a system fault handler if errors in the data transmission are detected to place the computer 21 and/or the surgical robotic system 10 into a safe state.

The computer 41 includes a plurality of controllers, namely, a main cart controller 41a, a setup arm controller 41b, a robotic arm controller 41c, and an instrument drive unit (IDU) controller 41d. The main cart controller 41a receives and processes joint commands from the controller 21a of the computer 21 and communicates them to the setup arm controller 41b, the robotic arm controller 41c, and the IDU controller 41d. The main cart controller 41a also manages instrument exchanges and the overall state of the mobile cart 60, the robotic arm 40, and the IDU 52. The main cart controller 41a also communicates actual joint angles back to the controller 21a.

Each of joints 63a and 63b and the rotatable base 64 of the setup arm 61 are passive joints (i.e., no actuators are present therein) allowing for manual adjustment thereof by a user. The joints 63a and 63b and the rotatable base 64 include brakes that are disengaged by the user to configure the setup arm 61. The setup arm controller 41b monitors slippage of each of joints 63a and 63b and the rotatable base 64 of the setup arm 61, when brakes are engaged or can be freely moved by the operator when brakes are disengaged, but do not impact controls of other joints. The robotic arm controller 41c controls each joint 44a and 44b of the robotic arm 40 and calculates desired motor torques required for gravity compensation, friction compensation, and closed loop position control of the robotic arm 40. The robotic arm controller 41c calculates a movement command based on the calculated torque. The calculated motor commands are then communicated to one or more of the actuators 48a and 48b in the robotic arm 40. The actual joint positions are then transmitted by the actuators 48a and 48b back to the robotic arm controller 41c.

The IDU controller 41d receives desired joint angles for the surgical instrument 50, such as wrist and jaw angles, and computes desired currents for the motors in the IDU 52. The IDU controller 41d calculates actual angles based on the motor positions and transmits the actual angles back to the main cart controller 41a.

The robotic arm 40 is controlled in response to a pose of the handle controller controlling the robotic arm 40, e.g., the handle controller 38a, which is transformed into a desired pose of the robotic arm 40 through a hand eye transform function executed by the controller 21a. The hand eye function, as well as other functions described herein, is/are embodied in software executable by the controller 21a or any other suitable controller described herein. The pose of one of the handle controllers 38a may be embodied as a coordinate position and roll-pitch-yaw (RPY) orientation relative to a coordinate reference frame, which is fixed to the surgeon console 30. The desired pose of the instrument 50 is relative to a fixed frame on the robotic arm 40. The pose of the handle controller 38a is then scaled by a scaling function executed by the controller 21a. In embodiments, the coordinate position may be scaled down and the orientation may be scaled up by the scaling function. In addition, the controller 21a may also execute a clutching function, which disengages the handle controller 38a from the robotic arm 40. In particular, the controller 21a stops transmitting movement commands from the handle controller 38a to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38a and is then passed by an inverse kinematics function executed by the controller 21a. The inverse kinematics function calculates angles for the joints 44a, 44b, 44c of the robotic arm 40 that achieve the scaled and adjusted pose input by the handle controller 38a. The calculated angles are then passed to the robotic arm controller 41c, which includes a joint axis controller having a proportional-derivative (PD) controller, the friction estimator module, the gravity compensator module, and a two-sided saturation block, which is configured to limit the commanded torque of the motors of the joints 44a, 44b, 44c.

Figure 5:
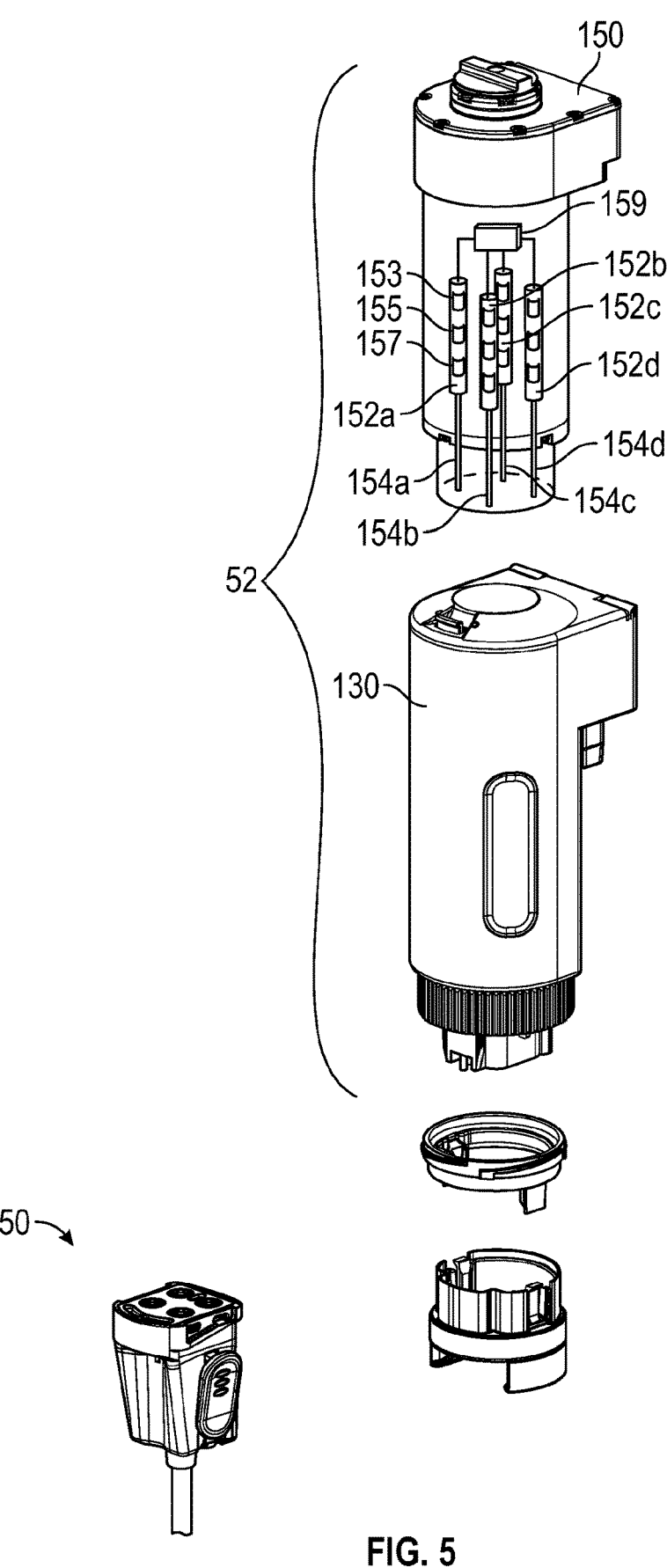
FIG. 5 is a perspective view, with parts separated, of an instrument drive unit and a surgical instrument according to an embodiment of the present disclosure.

With reference to FIG. 5, the IDU 52 is shown in more detail and is configured to transfer power and actuation forces from its motors 152a, 152b, 152c, 152d to the instrument 50 to drive movement of components of the instrument 50, such as articulation, rotation, pitch, yaw, clamping, cutting, etc. The IDU 52 may also be configured for the activation or firing of an electrosurgical energy-based instrument or the like (e.g., cable drives, pulleys, friction wheels, rack and pinion arrangements, etc.).

The IDU 52 includes a motor pack 150 and a sterile barrier housing 130. Motor pack 150 includes motors 152a, 152b, 152c, 152d for controlling various operations of the instrument 50. The instrument 50 is removably couplable to IDU 52. As the motors 152a, 152b, 152c, 152d of the motor pack 150 are actuated, rotation of the drive transfer shafts 154a, 154b, 154c, 154d of the motors 152a, 152b, 152c, 152d, respectively, is transferred to the drive assemblies of the instrument 50.

Figures 7, 8:
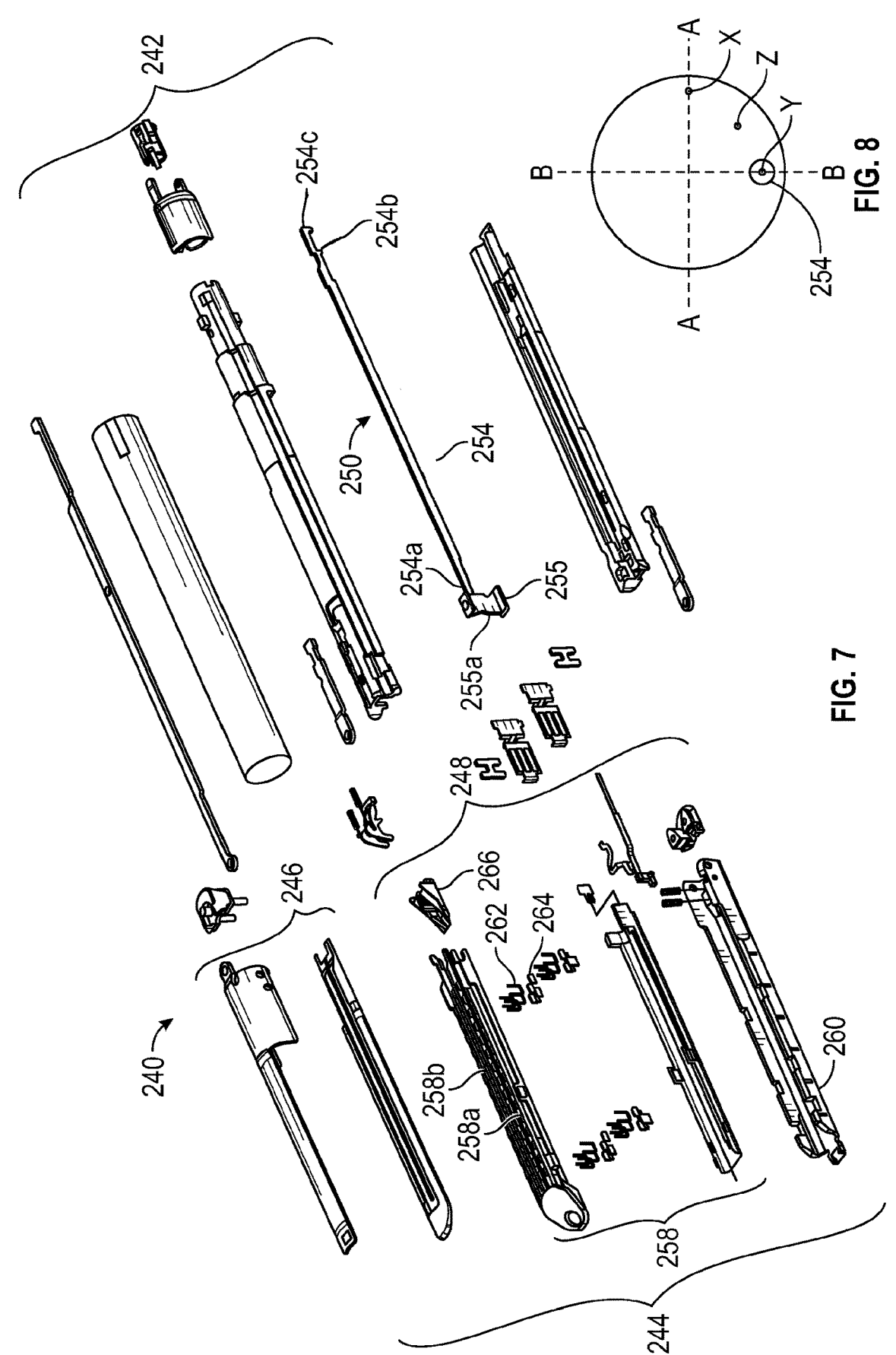
FIG. 7 is an enlarged, perspective view of an end effector of the surgical instrument of FIG. 6.
FIG. 8 is schematic, cross-sectional view of the end effector of the surgical instrument of FIG. 6.

The instrument 50 is configured to couple to a loading unit 240 secured to a distal end thereof. The instrument 50 is configured to transfer rotational forces/movement supplied by the IDU 52 (e.g., via the motors 152a, 152b, 152c, 152d of the motor pack 150) into longitudinal movement or translation of the cables or drive shafts to effect various functions of an end effector 244 (FIG. 7).

Each of the motors 152a, 152b, 152c, 152d includes a current sensor 153, a torque sensor 155, and an encoder 157. For conciseness only operation of the motor 152a is described below. The sensors 153, 155, 157 monitor the performance of the motor 152a. The current sensor 153 is configured to measure the current draw of the motor 152a and the torque sensor 155 is configured to measure motor torque. The torque sensor 155 may be any force or strain sensor including one or more strain gauges configured to convert mechanical forces and/or strain into a sensor signal indicative of the torque output by the motor 152a. The encoder 157 may be any device that provides a sensor signal indicative of the number of rotations of the motor 152a, such as a mechanical encoder or an optical encoder. Parameters which are measured and/or determined by the encoder 157 may include speed, distance, revolutions per minute, position, and the like. The sensor signals from sensors 153, 155, 157 are transmitted to the IDU controller 41d, which then controls the motors 152a, 152b, 152c, 152d based on the sensor signals. In particular, the motors 152a, 152b, 152c, 152d are controlled by an actuator controller 159, which controls torque outputted and angular velocity of the motors 152a, 152b, 152c, 152d. In embodiments, additional position sensors may also be used, which include, but are not limited to, potentiometers coupled to movable components and configured to detect travel distances, Hall Effect sensors, accelerometers, and gyroscopes. In embodiments, a single controller can perform the functionality of the IDU controller 41d and the actuator controller 159.

Figure 6:
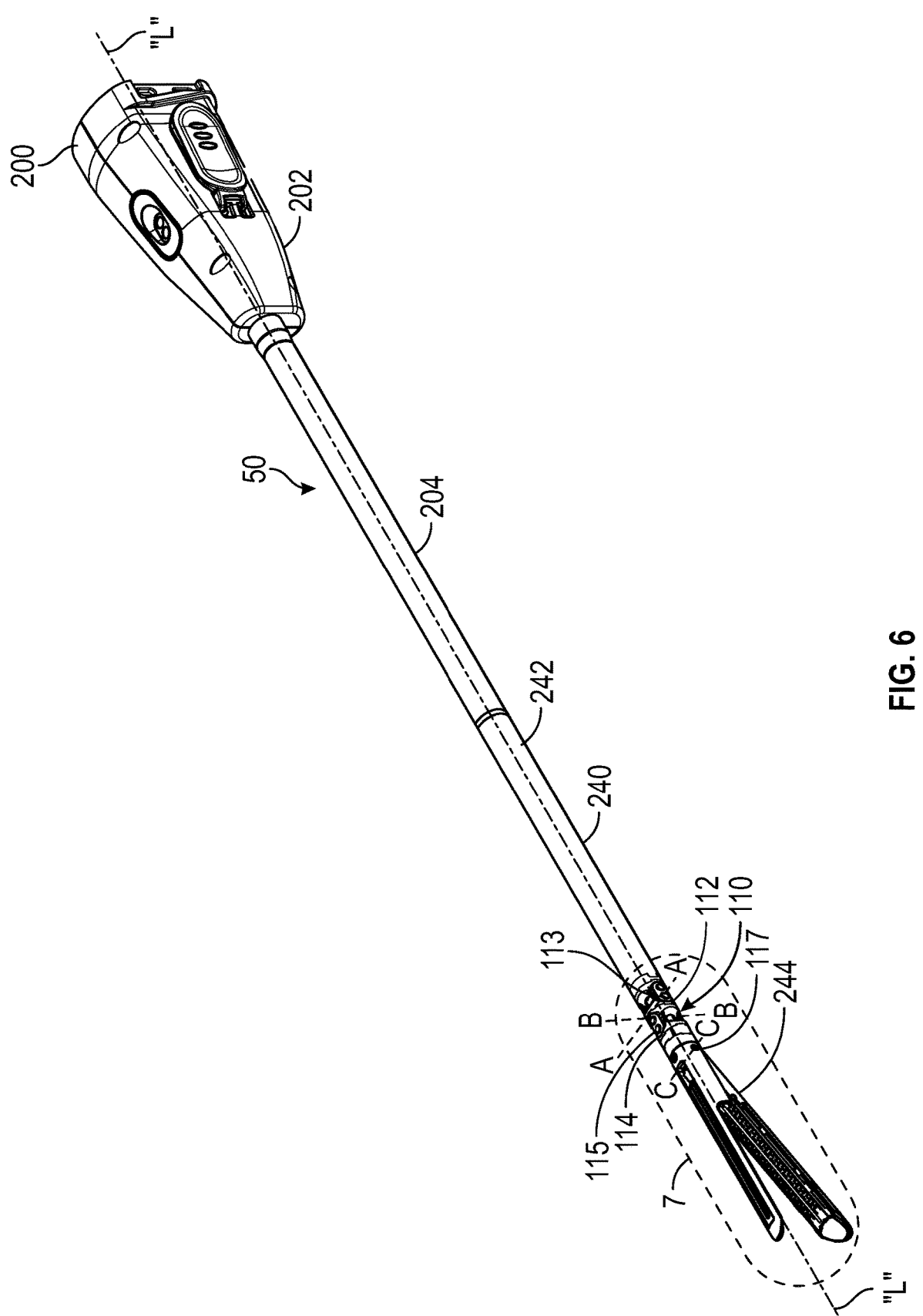
FIG. 6 is a perspective view of the surgical instrument of FIG. 5.

With reference to FIG. 6, instrument 50 includes an adapter 200 having a housing 202 at a proximal end portion thereof and an elongated shaft 204 that extends distally from housing 202. Housing 202 of adapter 200 is configured to selectively couple to IDU 52, to enable motors 152a, 152b, 152c, 152d of IDU 52 to operate the loading unit 240 coupled to the instrument 50. Housing 202 of adapter 200 supports a drive assembly that mechanically and/or electrically cooperates with motors 152a, 152b, 152c, 152d of IDU 52. Drive assembly 250 of instrument 50 may include any suitable electrical and/or mechanical component to effectuate driving force/movement.

Elongated shaft 204 is configured to couple to the loading unit 240 having an end effector 244. With reference to FIGS. 6 and 7, the loading unit 240 includes a proximal body portion 242 and the end effector 244. Proximal body portion 242 is releasably attached to a distal end portion of the instrument 50, and end effector 244 is pivotally attached to a distal end of proximal body portion 242. End effector 244 includes an anvil assembly 246 and a cartridge assembly 248. Anvil assembly 246 is pivotable in relation to the cartridge assembly 248 and is movable between an open or unclamped position and a closed or clamped position. Proximal body portion 242 includes a drive assembly 250.

Offset rod may be used in various end effector designs, such as wristed vessel sealers having two opposing seal plate jaws instead of a stapler. The offset rod may actuate the jaws and/or the knife. In both cases, the disclosed compensation algorithm may be used to assure the jaw or knife degree of freedom is decoupled from yaw/pitch of the end effector.

Another suitable end effector may be stitching instruments, (e.g., Covidien EndoStitch® or robotically controlled stitchers). In this design the instrument passes a needle between two opposing jaws. A small mechanism locks the needle into one of the two jaws and alternates jaws during suturing. One or more push/pull rods may be offset and their position or actuation distance adjusted based on the yaw/pitch of the end effector. Thus, in any instrument design, there may be multiple offset rods, in which case all of the offset rods may be compensated for yaw/pitch joint motion.

With reference to FIG. 6, the end effector 244 includes a joint 110 configured to allow for pivoting of the end effector 244 relative to the elongated shaft 204. The joint 110 may include a proximal portion 112 having a first pin 113 and a distal portion 114. The end effector 244 may be actuated using a plurality of cables (not shown) routed through proximal and distal portions 112 and 114 around their respective pulleys, which are integrally formed as arms of the proximal and distal portions 112 and 114. The proximal portion 112 along with the distal portion 114 and the anvil assembly 246 and the cartridge assembly 248 may be articulated about a first pivot (i.e., pitch) axis "A-A" to control a pitch angle of the end effector 244 with respect to a longitudinal axis "L-L". The end effector 244, namely, the distal portion 114 and the anvil assembly 246 and the cartridge assembly 248, may be articulated about a second pivot (i.e., yaw) axis "B-B" to control a yaw angle of the end effector 244 with respect to a longitudinal axis "L-L". The distal portion 114 includes a second pin 115 with the anvil assembly 246 and the cartridge assembly 248 pivotally coupled to the second pin 115. The anvil assembly 246 and the cartridge assembly 248 are configured to pivot about an axis "C-C" defined by a third pin 117 allowing for controlling a jaw angle between the anvil assembly 246 and the cartridge assembly 248. The yaw, pitch, and jaw angles are controlled by adjusting the tension and/or length and direction (e.g., proximal or distal) of the cables. Thus, the end effector 244 may have three degrees of freedom, yaw, pitch, and jaw angle between the anvil assembly 246 and the cartridge assembly 248. The three degrees of freedom, i.e., yaw, pitch, and jaw angle, are manipulated by applying varying amounts of tension to four drive cables of the instrument 50. Tension is applied to the drive cables by four individually addressable motors 152a-d in the IDU 52.

Drive assembly 250 includes a flexible drive rod 254 having a distal end portion 254a and a proximal engagement section 254b. With reference to FIG. 8, the drive rod 254 may have any suitable shape and may be offset from a neutral, i.e., central axis, of the end effector 244 in a manner described above. The distal end portion 254a includes an I-beam 255 having a knife 255a. The I-beam 255 is configured to travel through the anvil assembly 246 and the cartridge assembly 248, thereby pushing the anvil assembly 246 toward the cartridge assembly 248 to clamp tissue. The proximal engagement section 254b includes diametrically opposed inwardly extending fingers 254c that engage a drive member (not shown) of the instrument 50 to fixedly secure drive member to the proximal end of flexible drive rod 254. Drive rod 254 is actuated by the IDU 52.

Cartridge assembly 248 of end effector 244 includes a staple cartridge 258 removably supported in a carrier 260. Staple cartridge 258 defines a central longitudinal slot 258a, and a plurality of linear rows of staple retention slots 258b positioned on each side of the central longitudinal slot 258a. Each of the staple retention slots 258b receives a staple 262 and a portion of a staple pusher 264. During operation, drive assembly 250 abuts an actuation sled 266 and pushes actuation sled 266 through the staple cartridge 258. As the actuation sled 266 moves through staple cartridge 258, cam wedges of the actuation sled 266 sequentially engage staple pushers 264 to move staple pushers 264 vertically within staple retention slots 258b and sequentially eject the staples 262 therefrom for formation against an anvil plate 246a of anvil assembly 246. In addition, the drive rod 254 closes the anvil assembly 246 and the cartridge assembly 248 and simultaneously advances the knife 255a and the actuation sled 266. Once clamping, cutting, and stapling is completed, the drive rod 254 is retracted in a reverse (i.e., proximal) direction.

The drive rod 254 may be offset from one or both planes of adjustment. With reference to FIG. 8, the drive rod 254 may be positioned at location "y", as such the drive rod 254 is offset from pitch pivot axis "A-A", while being aligned with the yaw pivot axis "B-B". Thus, bending compensation is provided while the end effector 244 is articulated, i.e., pitched, about the pitch pivot axis "A-A". The drive rod 254 may also be disposed at location "x", at which the drive rod 254 is offset from the yaw pivot axis "B-B", while being aligned with the pitch pivot axis "A-A". Thus, bending compensation is provided while the end effector 244 is articulated about the yaw pivot axis "B-B". In further embodiments, the drive rod 254 may be disposed at location "z" in which the drive rod 254 is offset from both pivot axes "A-A" and "B-B." In this case, bending compensation is provided when the end effector 244 is articulated about either axis, i.e., pitch or yaw. Thus, application of the compensation method of the present disclosure depends on the offset of the drive rod 254 and is described below with respect only to a pitch axis "A-A." However, the compensation method may be modified to work with any number of pivot axes and offset position of the drive rod 254.

With reference to FIG. 9, a method for compensation for bending of the drive rod 254 may be implemented as software instructions executable by the controller 21a or any other suitable controller of the surgical robotic system 10. Initially, at step 300, the end effector 244 is pivoted in response to a pitch or yaw command from the surgeon console 30 or any other source. At step 301, the controller 21a determines whether drive rod 254 is affected by the pivot command, i.e., pivoting of the end effector 244 lengthens an actuation distance of the drive rod 254, since at described above, the drive rod 254 is bent further when it is offset from the neutral axis.

At step 302, the controller 21a determines a degree of rotation of the end effector 244 about a pivot axis from which the drive rod 254 is offset, e.g., at least one of the pitch pivot axis "A-A" or yaw pivot axis "B-B." The controller 21a may receive angle measurements from the encoder 157 of the motors 152a, 152b, 152c, 152d responsible for pivoting the end effector 244. In embodiments, articulation sensors (not shown) may be disposed within the proximal and distal portions 112 and 114 and/or the end effector 244, which provide angle measurements to the controller 21a.

At step 303, the controller calculates the bend radius of the drive rod 254 based on the angle of rotation, i.e., received angle measurements from step 302. At step 304, the controller 21a calculates the path length, i.e., the distance that the drive rod 254 is displaced by the pivoting of the end effector 244. The calculation determines the path length by using a portion of the circumference ($C=2\pi r$). At step 306, the controller 21a sets the compensation distance as the calculated path length, which is then used at step 308 to adjust the firing distance that the drive rod 254 travels to actuate the end effector 244, e.g., clamp, cut, staple, etc. The end effector 244 may be actuated after the compensation distance is calculated since actuation involves movement of the drive rod 254, which in the extended bent state may not fully actuate all of the mechanical components of the end effector. At step 310, during actuation, the drive rod 254 is advanced to the adjusted firing distance based on the compensation distance.

Figure 10:
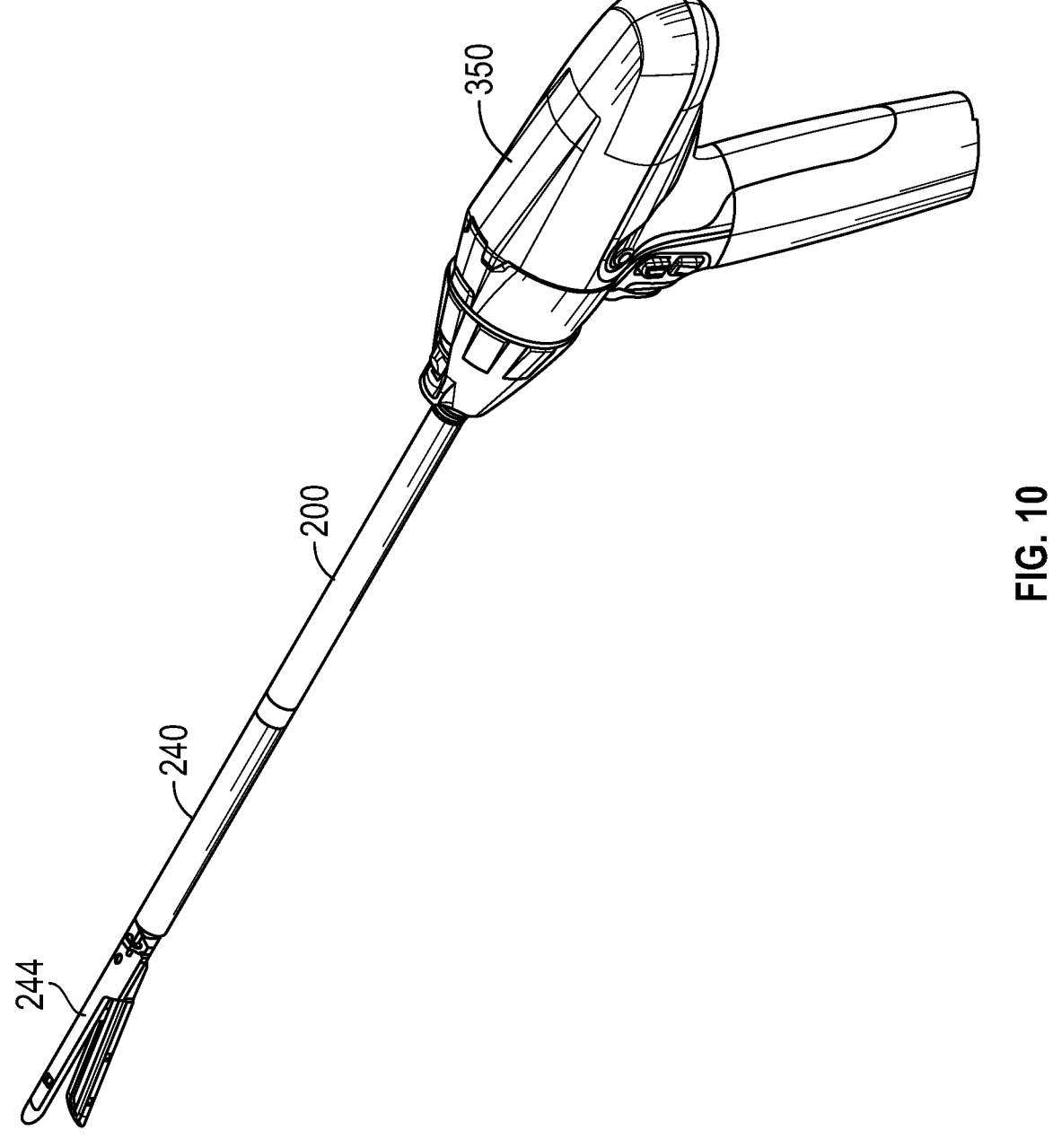
FIG. 10 is a perspective view of a powered surgical stapler according to an embodiment of the present disclosure.

With reference to FIG. 10, another embodiment of a powered surgical system includes a powered surgical handle 350, which includes similar components as the IDU 52, e.g., one or more motors, controllers, memory storing instructions, etc. The loading unit 240 may be used with a powered surgical handle 350. The handle 350 is configured to compensate for the offset flexible drive rod 254 in the similar manner described above.

Compensation algorithm may also be applied to a single port/multi-instrument designs or other flexible shaft instrument design. In these designs, the yaw/pitch/triangulation motion is developed by multiple stacked vertebrae in a series of articulating joints. If an offset rod was to be passed from the instrument housing all the way up to the end effectors, then the rod position would have to be compensated for the articulation of each of these "shoulder" and "elbow". The compensation would follow the same logic described above in FIG. 8. For these instruments, the offset rod could actuate the jaw aperture (i.e., seal plates for a vessel sealer), or a vessel sealer knife, or a stapling firing, etc.

In embodiments, the controller 21a is also configured to compensate for the force applied to the mechanism during pushing and pulling around the bend. This is secondary to compensating for the change in length due to bend radius. A calculated compensation parameter is calculated to determine stiffness of mechanism, i.e., drive rod 254 and then apply a distance compensation that is proportional to the force measured on the mechanism. The compensation is a linear compensation where distance=force*calculated stiffness parameter.

In further embodiments, the mechanism is tested under different loads to derive the stiffness parameter and/or specific compensation equation. As above, this equation would give the robot or powered instrument a second compensation amount to add to the bend radius compensation.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. A surgical robotic system comprising:
a surgeon console configured to receive user input;

a robotic arm configured to hold an instrument drive unit and an instrument coupled to the instrument drive unit, the instrument controllable in response to the user input, the instrument including:

an elongate shaft;

an end effector coupled to the elongate shaft at a joint, the end effector being configured to pivot about at least one pivot axis relative to the elongate shaft; and a flexible drive rod configured to move longitudinally through the joint and to actuate at least one function of the end effector, the flexible drive rod being disposed off-axis relative to at least one pivot axis of the joint; and a controller configured to:

calculate a bend radius of the flexible drive rod during pivoting of the end effector;

calculate a compensation distance based on the bend radius; and command the instrument drive unit to advance the flexible drive rod by an actuation distance adjusted by the compensation distance.

2. The surgical robotic system according to claim 1, wherein the controller is further configured to calculate the bend radius based on an angle of the pivoting of the end effector.

3. The surgical robotic system according to claim 2, wherein the instrument drive unit is configured to measure the angle of the pivoting of the end effector.

4. The surgical robotic system according to claim 1, wherein the controller is further configured to receive the user input including a command for pivoting the end effector and to determine whether the command lengthens the actuation distance of the flexible drive rod.

5. The surgical robotic system according to claim 1, wherein the end effector is a surgical stapler including an anvil and a cartridge having a plurality of staples.

6. The surgical robotic system according to claim 5, wherein the flexible drive rod, during longitudinal advancement, is configured to approximate the anvil relative to the cartridge.

7. The surgical robotic system according to claim 5, wherein the flexible drive rod, during longitudinal advancement, is configured to eject the plurality of staples from the cartridge.

8. A powered surgical system comprising:

an instrument drive unit;

an instrument coupled to the instrument drive unit, the instrument including:

an elongate shaft;

an end effector coupled to the elongate shaft at a joint, the end effector is configured to pivot about at least one pivot axis relative to the elongate shaft; and a flexible drive rod configured to move longitudinally through the joint and to actuate at least one function of the end effector, the flexible drive rod being disposed off-axis relative to at least one pivot axis of the joint; and a controller configured to:

calculate a bend radius of the flexible drive rod during pivoting of the end effector;

calculate a compensation distance based on the bend radius; and command the instrument drive unit to advance the flexible drive rod by an actuation distance adjusted by the compensation distance.

9. The powered surgical system according to claim 8, wherein the controller is further configured to calculate the bend radius based on an angle of the pivoting of the end effector.

10. The powered surgical system according to claim 9, wherein the instrument drive unit is configured to measure the angle of the pivoting of the end effector.

11. The powered surgical system according to claim 8, wherein the controller is further configured to receive a command for pivoting the end effector and to determine whether the command lengthens the actuation distance of the flexible drive rod.

12. The powered surgical system according to claim 8, wherein the end effector is a surgical stapler including an anvil and a cartridge having a plurality of staples.

13. The powered surgical system according to claim 12, wherein the flexible drive rod, during longitudinal advancement, is configured to approximate the anvil relative to the cartridge.

14. The powered surgical system according to claim 12, wherein the flexible drive rod, during longitudinal advancement, is configured to eject the plurality of staples from the cartridge.

15. A method for controlling a powered surgical system, the method comprising:

pivoting an end effector coupled to an elongate shaft of an instrument at a joint about at least one pivot axis relative to the elongate shaft;

calculating a bend radius of a flexible drive rod during pivoting of the end effector, the flexible drive rod configured to move longitudinally through the joint and to actuate at least one function of the end effector, the flexible drive rod being disposed off-axis relative to at least one pivot axis of the joint;

calculating a compensation distance based on the bend radius; and controlling an instrument drive unit coupled to the instrument to advance the flexible drive rod by an actuation distance adjusted by the compensation distance.

16. The method according to claim 15, further comprising:

calculating the bend radius based on an angle of the pivoting of the end effector.

17. The method according to claim 16, further comprising:

measuring the angle of the pivoting of the end effector.

18. The method according to claim 15, further comprising:

receiving a command for pivoting the end effector and determining whether the command lengthens the actuation distance of the flexible drive rod.

19. The method according to claim 15, wherein the end effector is a surgical stapler including an anvil and a cartridge having a plurality of staples.

20. The method according to claim 19, further comprising:

advancing the flexible drive rod to approximate the anvil relative to the cartridge and to eject the plurality of staples from the cartridge.

* * * * *